(12) United States Patent
Bharat et al.

(10) Patent No.: US 10,286,228 B2
(45) Date of Patent: May 14, 2019

(54) REAL-TIME FUSION OF ANATOMICAL ULTRASOUND INFORMATION AND RADIATION DELIVERY INFORMATION FOR RADIATION THERAPIES

(71) Applicant: KONINKLIJKE PHILIPS N.V., Eindhoven (NL)

(72) Inventors: Shyam Bharat, Arlington, MA (US); Ehsan Dehghan Marvast, New York, NY (US); Ameet Kumar Jain, New York, NY (US); Amir Mohammad Tahmasebi Maraghoosh, Ridgefield, CT (US); Francois Guy Gerard Marie Vignon, Croton on Hudson, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 241 days.

(21) Appl. No.: 15/102,333

(22) PCT Filed: Dec. 5, 2014

(86) PCT No.: PCT/IB2014/066616
§ 371 (c)(1),
(2) Date: Jun. 7, 2016

(87) PCT Pub. No.: WO2015/087217
PCT Pub. Date: Jun. 18, 2015

(65) Prior Publication Data
US 2016/0310760 A1 Oct. 27, 2016

Related U.S. Application Data

(60) Provisional application No. 61/915,081, filed on Dec. 12, 2013.

(51) Int. Cl.
*A61B 6/03* (2006.01)
*A61N 5/10* (2006.01)
(Continued)

(52) U.S. Cl.
CPC ............ *A61N 5/1039* (2013.01); *A61B 6/032* (2013.01); *A61B 8/0833* (2013.01);
(Continued)

(58) Field of Classification Search
USPC .................................................. 600/411, 431
See application file for complete search history.

(56) References Cited

U.S. PATENT DOCUMENTS 5,810,007 A 9/1998 Holupka et al.
7,575,550 B1 8/2009 Govari
(Continued)

FOREIGN PATENT DOCUMENTS

EP 1374791 A1 1/2004
JP 2002514459 A 5/2002
(Continued)

OTHER PUBLICATIONS

Bohme, M., "Innovative Tracking and Navigation Technology in Medicine", amedo Smart Tracking Solutions, 2010.
(Continued)

*Primary Examiner* — Nicole F Lavert

(57) ABSTRACT

A radiation therapy delivery system (10) includes an ultrasound imaging unit (26), a radiation therapy delivery mechanism (12, 56, 70, 88), a plurality of fiducials (22, 90) located internal to the subject, an image fusion unit (40), and a delivery evaluation unit (38). The ultrasound imaging unit (26) includes a transducer (30) that emits ultrasonic sound waves to image in real-time an anatomic portion of a subject (16) in a first coordinate system. The radiation therapy delivery mechanism (12, 56, 70, 88) delivers amounts of therapeutic radiation in the anatomic portion of the subject in a second coordinate system. The fiducials (22, 90) include implants or a trans-rectal ultrasound probe (80). The image fusion unit (40) registers locations of the plurality of fidu-
(Continued)

cials to at least one of the first and the second coordinate system and tracks the locations of the fiducials in real-time. The delivery evaluation unit (38) identifies locations and the amounts of delivered therapeutic radiation relative to the imaged real-time anatomic portion of the subject.

15 Claims, 10 Drawing Sheets

(51) Int. Cl.
  *A61B 8/08* (2006.01)
  *A61B 8/00* (2006.01)
  *A61B 90/00* (2016.01)
(52) U.S. Cl.
  CPC ............ *A61B 8/4483* (2013.01); *A61B 8/483* (2013.01); *A61N 5/1038* (2013.01); *A61N 5/1067* (2013.01); *A61B 2090/3929* (2016.02); *A61N 2005/1051* (2013.01); *A61N 2005/1058* (2013.01); *A61N 2005/1061* (2013.01)

(56) References Cited

U.S. PATENT DOCUMENTS

| | | | |
|---|---|---|---|
| 8,452,375 B2 | 5/2013 | Krag et al. | |
| 8,605,964 B2 | 12/2013 | Fichtinger et al. | |
| 2004/0138555 A1* | 7/2004 | Krag | A61B 17/32053 600/424 |
| 2009/0124871 A1 | 5/2009 | Arshak et al. | |
| 2010/0268072 A1 | 10/2010 | Hall et al. | |
| 2011/0009742 A1 | 1/2011 | Lachaine et al. | |
| 2012/0071758 A1* | 3/2012 | Lachaine | A61B 8/085 600/439 |
| 2013/0237822 A1 | 9/2013 | Gross et al. | |
| 2015/0038765 A1 | 2/2015 | Vilsmeier | |

FOREIGN PATENT DOCUMENTS

| | | |
|---|---|---|
| JP | 2005514969 A | 5/2005 |
| JP | 2008532568 A | 8/2008 |
| WO | 0209588 | 2/2002 |
| WO | 0239917 A1 | 5/2002 |
| WO | 2008051749 A2 | 5/2008 |

OTHER PUBLICATIONS

Mung, J., "A non-disruptive technology for robust 3D tool tracking for US guided Interventions", MICCAI vol. 14 (Pt.1) pp. 153-50, 2011.

\* cited by examiner

REAL-TIME FUSION OF ANATOMICAL ULTRASOUND INFORMATION AND RADIATION DELIVERY INFORMATION FOR RADIATION THERAPIES

CROSS-REFERENCE TO PRIOR APPLICATIONS

This application is the U.S. National Phase application under 35 U.S.C. § 371 of International Application Serial No. PCT/IB2014/066616, filed on Dec. 5, 2014, which claims the benefit of U.S. Application Ser. No. 61/915,081, filed on Dec. 12, 2013. These applications are hereby incorporated by reference herein.

BACKGROUND

The following relates generally to medical imaging and radiation therapy. It finds particular application in conjunction with real-time imaging of anatomical information using ultrasound and delivery of radiation therapy, and will be described with particular reference thereto. However, it will be understood that it also finds application in other usage scenarios and is not necessarily limited to the aforementioned application.

Radiation therapy is a procedure which uses radiation to treat a patient, often to kill or destroy harmful tissues, e.g. tumors. Radiation therapy is applied to the tissues of a subject to minimize radiation to healthy tissues. Healthy tissues can include organs at risk (OARs) such as a heart, liver, kidneys, urethra, rectum, bladder, etc. which may be in close proximity to or include unhealthy tissue. Precise placement of radiation during delivery is important to preserve functioning organs while destroying the unhealthy or diseased tissue. Two conventional radiation therapy techniques include brachytherapy and external beam radiation therapy (EBRT). Anatomical images for planning of radiation therapy typically use X-ray computed tomography (CT) which provides detailed anatomical information, but uses x-ray radiation to obtain the anatomical images.

Brachytherapy typically uses low dose radiation point sources or seeds which are implanted in unhealthy tissues of the subject. The seeds are distributed or dropped through a needle inserted into the unhealthy tissue to provide radiation to surrounding unhealthy tissue. The seeds provide a localized source of radiation. Typically, 50-100 seeds can be implanted into the prostate. Brachytherapy is commonly used for treatment of breast, cervical, prostate, and skin cancers. Precise placement or delivery of the seeds relative to the unhealthy and OARs determines the dose of radiation delivered to the tumor and the OARs. Multiple seeds are distributed in the unhealthy tissue to provide coverage. The coverage is based on the location of each dropped seed and the amount of radiation emitted by each point source.

EBRT delivers external linear beams of radiation through the body to the target tissues, using a EBRT device such as a linear accelerator (LINAC). Typically, the beams can be shaped and aimed from different directions to help avoid striking OARs. Knowing the precise position of the target and OARs relative to the radiation beam when the external radiation beam is active determines the dose delivery to both the tumor and any healthy tissues in the path of the radiation beam.

In the delivery of radiation therapy, the precise placement of the radiation relative to the anatomical locations of unhealthy and healthy tissue affects the outcome, particularly the sufficiency of the dose to kill the unhealthy tissue and the side effects of the dose to the healthy tissue. During the delivery of radiation, the location of the healthy and unhealthy tissue is subject to movement of the patient. The movement can include rigid movement, non-rigid movement, deformation of organs, and repetitive movement due to respiration and/or cardiac cycles. One challenge is matching the location of the therapeutic radiation during delivery to the anatomical location of the target and OARs. In other words, one challenge is to register the dosimetric information and anatomical information in a common coordinate system during delivery. A second challenge is measuring the motion accurately in substantially real time such that adjustments can be made during the delivery to correct for position and/or motion.

For example, in brachytherapy, anatomical information can be obtained from ultrasound, but matching the location of the dropped seeds with the target and OARs can be problematic. Ultrasound (US) can provide continuous real-time anatomical images during delivery of therapeutic radiation without using x-ray radiation. However, visibility of seeds can be obscured or confused with shadowing or other artifacts, which leads to poor sensitivity and specificity. Poor placement of seeds can lead to cold spots or areas where the target is not receiving the proper radiation dose or has spots where OARs receive more than prescribed.

One approach has been to take intermediate CT images which contrast the seeds with less visibility to organ boundaries in high contrast, but which involves moving the patient from a brachytherapy operative configuration to a CT imaging configuration and returning the patient back to the operative environment to make adjustments for seed placement. The two patient movements are apt to create registration errors between the CT and brachytherapy coordinate systems. The use of CT also adds additional x-ray dose to the patient.

Another approach is the use of intermittent fluoroscopic images which images the seeds with good contrast and reduces the x-ray imaging dose to the patient compared to CT. However, fluoroscopic images provide less anatomic contrast and are taken intermittently, which makes matching of seed locations to the anatomic locations difficult.

In EBRT, beams of radiation are directed through the subject. Typically external markers placed on the patient's skin are used to register the patient to the coordinate system of the EBRT delivery device and the coordinate system of high resolution planning images. However, the external marks provide poor internal anatomic information. Due to tissue pliability, registration errors between the external markers and the target and OARs can occur. Without precise anatomic information in a common coordinate system with the external beam coordinate system during delivery of radiation, incomplete dose coverage of the tumor and significant damage to OARs can result. One approach to protecting OARs is to exclude radiation delivery from a margin around OARs large enough to include the entire range of motion. One approach to assuring delivery of the prescribed dose is to irradiate a margin around the target such that the target is in the beam over the range of motion. Due to proximity of the target and OARs, assuring full dose to the target and minimal dose to OARs are often conflicting goals.

Another approach to identifying the precise location of the organ boundaries and/or motion is the use of electromagnetic (EM) tracking technology. However, EM tracking is sensitive to external distortions such as metallic equipment, prostheses in patients, pacemakers, etc., and depends on positioning of the EM field generator.

SUMMARY

The following discloses a new and improved real-time fusion of anatomical ultrasound information and radiation delivery information for radiation therapies which addresses the above referenced issues, and others.

In accordance with one aspect, a radiation therapy system includes a plurality of fiducials located internal to a subject, an ultrasound imaging unit, a radiation planning unit, and an image fusion unit. The ultrasound imaging unit includes a transducer that emits ultrasonic sound waves to image in real-time an anatomic portion of a subject in a real-time coordinate system. The radiation planning unit includes at least one radiation treatment planning image identifying the planned locations and amounts of therapeutic radiation in the anatomic portion of the subject according to a planning coordinate system. The image fusion unit registers the real-time coordinate system to the planning coordinate system based on the locations of the internal fiducials and tracks the locations of the fiducials in real-time.

In accordance with another aspect, a radiation therapy delivery system includes an ultrasound imaging unit, a radiation therapy delivery mechanism, a plurality of fiducials located internal to the subject, an image fusion unit, and a delivery evaluation unit. The ultrasound imaging unit includes a transducer that emits ultrasonic sound waves to image in real-time an anatomic portion of a subject in a first coordinate system. The radiation therapy delivery mechanism delivers amounts of therapeutic radiation in the anatomic portion of the subject in a second coordinate system. The fiducials include implants or a trans-rectal ultrasound probe. The image fusion unit registers locations of the plurality of fiducials to at least one of the first and the second coordinate system and tracks the locations of the fiducials in real-time. The delivery evaluation unit identifies locations and the amounts of delivered therapeutic radiation relative to the imaged real-time anatomic portion of the subject.

In accordance with another aspect, a method of radiation therapy includes generating real-time ultrasound images with a transducer which emits ultrasonic sound waves in an anatomic portion of a subject in a first coordinate system which includes a plurality of internal fiducial locations. Therapeutic radiation is delivered in locations and amounts of the portion of the subject in a second coordinate system. Locations of the plurality of fiducials are identified. The locations of the plurality of fiducials are registered to at least one of the first and the second coordinate system and the locations of the fiducials are tracked in real-time. Locations and amounts of therapeutic radiation delivered to the anatomic portion of the subject are determined.

In accordance with another aspect, an implanted fiducial includes a wireless transmitter, a sensor connected to the transmitter, and a capsule constructed of biocompatible material which encapsulates the wireless transmitter and the sensor and configured to be implanted in a subject through a needle inserted into the subject. The wireless transmitter transmits at least a self-identity. The sensor includes a piezoelectric element activated in response to receiving emitted ultrasonic sound waves and powers the transmitter.

In accordance with another aspect, an ultrasound system includes a trans-rectal probe, a processor, and a display device. The probe includes a shaft with a rounded end configured for insertion into a rectum of the subject, at least one imaging array located on the shaft and includes an emitter which emits ultrasonic sound waves and receive reflected sound waves, and a plurality of radio-opaque fiducials positioned relative to the shaft and positioned in different orientations to provide a three dimensional coordinate reference calibrated to the ultrasound imaging unit coordinate system. The processor is connected to the at least one imaging array and programmed to reconstruct the received reflected sound waves into anatomic images. The display device is configured to display the reconstructed anatomic images.

One advantage is the union of continuous real-time anatomic information with the radiation therapy delivery information in a common coordinate system.

Another advantage resides in ability to adjust delivery of therapeutic radiation during delivery based on positions of the radiation source, the unhealthy tissue and/or the healthy tissue.

Another advantage resides in use of a non-x-ray imaging source for continuous real-time anatomic imaging information.

Another advantage resides in precise internal patient motion tracking during radiation delivery.

Another advantage resides in registering the coordinate system of the radiation source, the coordinate system of a diagnostic image, and a coordinate system of patient anatomy in real time.

Another advantage resides in providing the clinician the ability to confirm if his/her interpretation of one imaging modality (e.g., US) is correct, by fusing information with another imaging modaility (e.g., fluoroscopy) whenever deemed necessary.

Still further advantages will be appreciated to those of ordinary skill in the art upon reading and understanding the following detailed description.

BRIEF DESCRIPTION OF THE DRAWINGS

The invention may take form in various components and arrangements of components, and in various steps and arrangement of steps. The drawings are only for purposes of illustrating the preferred embodiments and are not to be construed as limiting the invention.

DETAILED DESCRIPTION

Figure 1:
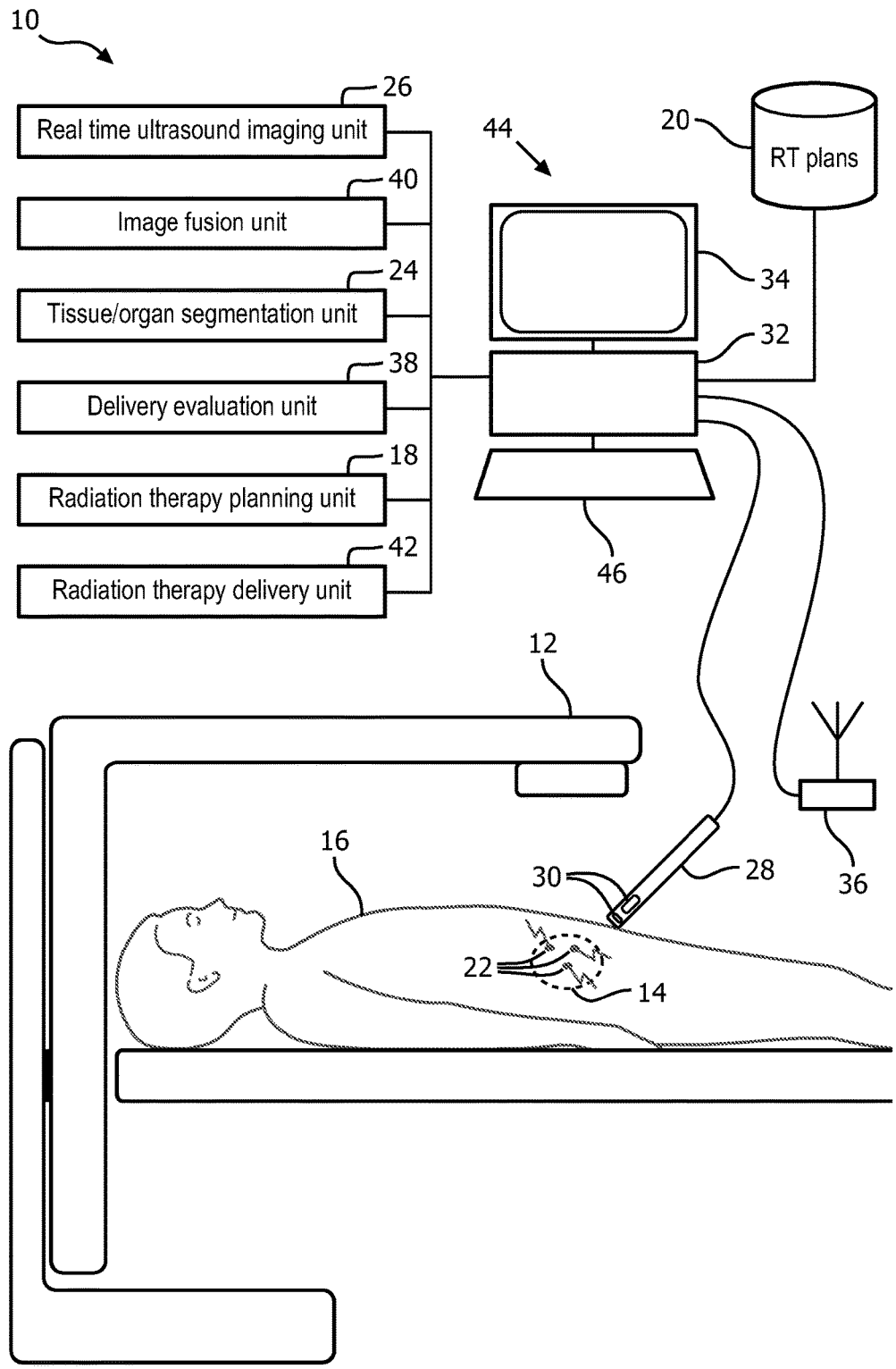
FIG. 1 schematically illustrates an embodiment of a real-time fusion or registration of anatomical ultrasound information and radiation delivery system configured for EBRT.

With reference to FIG. 1, an embodiment of a real-time fusion of anatomical ultrasound information and radiation delivery information system 10 configured for EBRT is schematically illustrated. The system is shown using a radiation therapy configuration for EBRT with an EBRT device 12 directed toward a prostate 14 of a subject 16. A radiation therapy planning unit 18 images the subject and stores a planning image of the subject as part of the radiation therapy plan 20. The planning image can be obtained from a CT image, MR image, and the like. The planning image is used to construct the radiation therapy plan 20 which includes the instructions for placement of radiation delivery to anatomic portions of the subject. The planning image can include internal or implanted fiducials 22 present in the planning image and aid in registering the planning image to the radiation delivery and real time anatomic information.

The radiation therapy planning unit 18 maintains the radiation therapy plan 20. The radiation therapy plan 20 identifies the planned delivery locations or targets of therapeutic radiation. For fractionated treatments, intermediate CT or other planning images can be co-registered with the fiducials 22.

A segmentation unit 24 segments target tissues such as a tumor. The segmentation unit 24 can segment one or more healthy tissues such as OARs in the anatomic imaging region such as the prostate. Other healthy tissues in close proximity to the therapeutic radiation such at the urethra, bladder, etc. can be segmented.

The system includes an ultrasound imaging unit 26 which images an anatomic portion of the subject in continuous real-time. The ultrasound imaging unit can be configured with a 2-dimensional imaging (2D) or a 3-dimensional imaging (3D) imaging probe 28. Robotic control and rotation can be used for a 2D imaging probe. The ultrasound imaging unit operates in a first coordinate system. The first coordinate system can be registered to a room coordinate system through means known in the art, such as video, laser, acoustic, and the like. For example, the probe 28 can be marked with markers visible to a plurality of cameras calibrated to the room which provide the position of the probe relative to room coordinates.

The ultrasound imaging probe 28 includes at least one transducer 30, which emits sound waves at an ultrasonic frequency into the tissues of the subject. The sound waves can be emitted according to a sound frequency, direction, duration, timing, and angle. The sound waves are reflected and received at the transducer. The transducer 30 connects to one or more processors 32 of the ultrasound imaging unit 26 which converts signals transmitted by the transducer to the processor 32 indicative of the received reflected sound waves to images. The images are displayed on a display device 34. Segmented tissues can be color coded or otherwise indicated in the displayed ultrasound images based on co-registration with the planning image. The probe 28 can be applied externally, such transperineally or transabdominally as shown, or applied internally such as inserted into a rectum or an esophagus.

The EBRT delivery device 12 can include a LINear ACcelerator (LINAC), x-ray, particle beam devices, and the like. The EBRT delivery device 12 delivers radiation therapy in linear beams projected through the tissues of the subject 16 according to a second coordinate system. The beams can be shaped through the use of multi-leaf collimators (MLCs). The beams can be gated on and off. The beams can be projected from different angles about the subject based on the radiation therapy plan 20. The instructions for the EBRT device 12 are executed by the radiation therapy delivery unit 32, which control the precise location, intensity, duration, and shape of the external radiation therapy beam. The coordinate system of the EBRT device can be calibrated to the coordinate system of the room.

The fiducials 22 are internally located and can be implanted. The fiducials 22 as shown are implanted in an abdominal region, but can be implanted in any anatomic region. The fiducials 22 can be configured with a radiation point source, such as in combined EBRT and brachytherapy, or without the radiation point source as illustrated. The implanted fiducials 22 provide for motion tracking and coordinate reference. For example, fiducials can be implanted in the prostate and along surfaces of surrounding OARs such as the rectal wall, urethra, bladder, etc. As the subject respires the prostate and/or OARs can move and/or deform. The fiducials provide boundary information which reduces or eliminates the margin typically used to accommodate motion.

The fiducials 22 are encapsulated in a biocompatible capsule to form seeds. The fiducials 22 wirelessly transmit a self-identity when activated in response to receiving the ultrasound sound waves. For example, each fiducial can be configured with an alphanumeric designator. A first fiducial transmits a unique identity of A00001, and a second fiducial transmits a unique identity of A00002, etc. Alternatively, the fiducials can be transmit the self-identity based on a predetermined radio frequency. The fiducials 22 can be configured with additional circuitry to transmit additional information. For example, the transmitted additional information can include a particular ultrasound frequency activation emitted at certain angles or intensity measure by the transducer and received by the fiducial. In another example, the transmitted additional information can include a checksum or other information which verifies the self-identity or a cycle count which establishes a time currency for the transmission.

An antenna 36 located external to the subject receives the transmitted information from the fiducials 22. The antenna communicates the received signals to an image fusion unit 38 which locates the corresponding fiducial in the first coordinate system of the ultrasound imaging unit 26. The image fusion unit fuses the location of the fiducials to the first coordinate system by analyzing the emitted ultrasound signals received by the fiducial as the emitted signals sweep the field of view. Time-of-flight measurements provide the axial or radial distance of the fiducial 22 from the emitter 30. Amplitude measurements and order in a beam firing sequence provide lateral or angular position of the fiducial. When used with 3-D transducers or 2-D matrix arrays, the elevation of the fiducial is obtained. Based on the timing of the received fiducial self-identity and the firing sequence of the ultrasound probe, the location of the fiducial 22 can be determined relative to the transducer 30 or in the coordinate system of the continuous real-time ultrasound imaging unit 26.

The image fusion unit 40 fuses the first coordinate system of the continuous real-time imaging unit 26 which contains the anatomic information, e.g. prostate region with the second coordinate system of the therapeutic radiation delivery device 12 which delivers therapeutic radiation, e.g. EBRT device linear beams of therapeutic radiation, based on the fiducials 22. The fusion unit can additionally register the planning image of the radiation plan 20 to the fused coordinate system. The fiducials provide accurate location within the anatomic region and provide precise motion information not possible with external fiducials. Through the fused coordinate system, the precise location of the anatomic information of the ultrasound images and planning images is known to the radiation therapy delivery device.

A delivery evaluation unit 42 receives the amount and location of the therapeutic radiation delivered based on the beam shape, duration, and direction from the EBRT device according to the EBRT coordinate system. The delivery evaluation unit 42 determines the amount and location of the therapeutic radiation delivered to each of the target and OARs based on the fused coordinate system. The delivery evaluation unit 42 tracks the position of the fiducials relative to the radiation beam. The tracking can include segmentation information from the planning information and/or entered information concerning tissue boundaries, OARs, targets, etc. relative to the implanted fiducials.

The radiation planning unit 18 can modify the set of instructions during delivery based on positions of the targets or the OARs relative to the delivered beams of therapeutic radiation according to the fused coordinate system. For example, the radiation delivery unit can be controlled to gate the radiation beam when the target tissue moves out of the radiation beam and/or OARs move into the radiation beam. In another example, the MLC can adaptively move to shape the beam to conform to the movement of the target and/or OARs based on the movement of the fiducials. Another example combines the gating on and off with the adaptive MLC movement based on the distance of repetitive motion. The MLC can be used to adapt to repetitive motion within specific parameters which if exceeded gate the beam off.

The delivery evaluation unit 38 accumulates therapeutic radiation doses received by the OARs and target tissues using the fiducials as reference. For example, the accumulated radiation is accumulated continuously in real-time. Adjustments can be made in the delivery based on the accumulated dose. The dose can be accumulated across multiple treatment fractions and/or combined with brachytherapy dose information, e.g. internal therapeutic radiation. The accumulated doses can be further used to modify the delivery. For example, the MLC can shape the beam further for healthy tissues, based on movement of the tissues into and out of the beam, and receive a threshold amount during the current treatment delivery.

The processor 32 and the display device 34 can be configured as part of a workstation 44. The healthcare practitioner can interact with controls, enter commands, etc. using at least one input device 46 such as a keyboard, mouse, microphone, and the like. The processor 20 includes one or more electronic processors or electronic processing device. The display 24 displays the continuous real-time ultrasound images, superimposed images or image overlays, menus, panels, and user controls. The workstation 44 can be a desktop computer, a laptop, a tablet, a mobile computing device, a smartphone, and the like.

The various units 18, 24, 26, 38, 40, and 42 are suitably embodied by a programmed or configured electronic data processing device, such as the electronic processor or electronic processing device 32 of the workstation 44, or by a network-based server computer operatively connected with the workstation 44 by a network, or so forth. The disclosed fusion, location, segmentation, evaluation and delivery techniques are suitably implemented using a non-transitory storage medium storing instructions (e.g., software) readable by an electronic data processing device and executable by the electronic data processing device to perform the disclosed techniques.

Figure 2A:
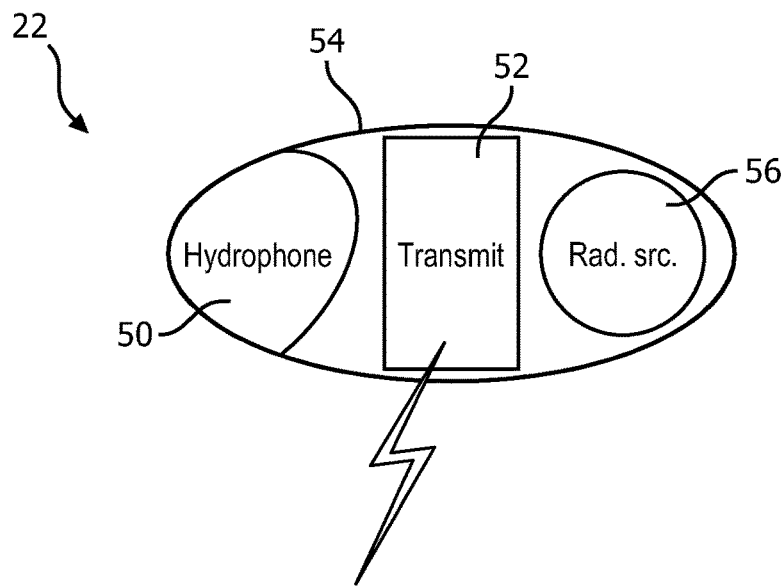
FIGS. 2A-2B schematically illustrates embodiments of internal fiducials.
Figure 2B:
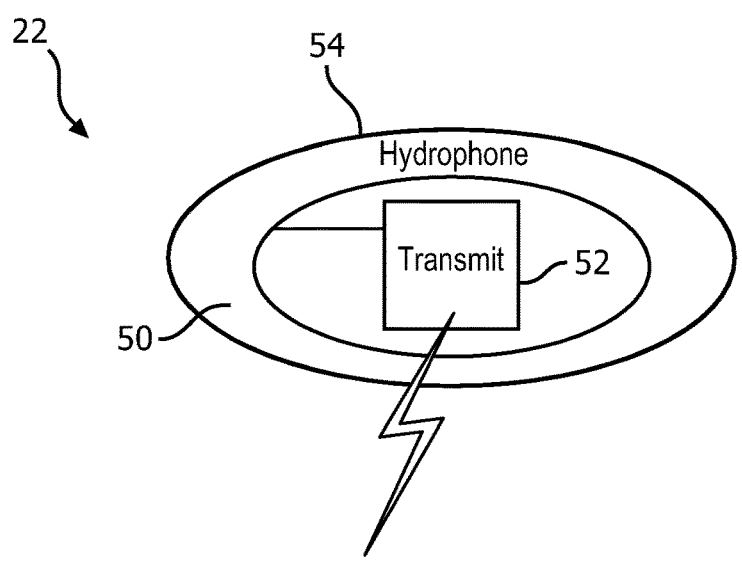

With reference to FIGS. 2A and 2B embodiments of internal fiducials 22 are schematically illustrated. In FIG. 2A, the fiducial 26 includes a hydrophone or sensor 50 connected to a wireless transmitter 52, and a capsule 54 constructed of biocompatible material which encapsulates the sensor 50, the transmitter 52, and a radiation point source 56 for use in brachytherapy. The sensor 50 includes a piezoelectric element activated in response to receiving the emitted ultrasonic sound waves and powers the transmitter 52. The piezoelectric element of the sensor can be incorporated into a portion or all of the surface of the capsule. The sensor can include lead zirconium titanate (PZT), polyvinylidenefluoride (PVDF), a copolymer, or other piezoelectric material. The sensor is about 0.2 mm in size. The capsule 54 is configured cylindrically to be implanted in the subject through a needle inserted into the subject. The capsule is sized and shaped to feed through the interior of the needle and drop into a location internal to the body of the subject at the tip of the needle. The radiation point source 56 functions as a brachytherapy seed.

The fiducial 26 illustrated in FIG. 2B includes the sensor 50, wireless transmitter 52, and the capsule 54. In the configuration of FIG. 2B, the sensor can cover substantially the entire surface of the capsule. The circuitry of the transmitter can include limited processing. For example, in addition to transmitting the self-identity or other information, the circuitry can process the received ultrasound sound waves to partially or fully estimate the position in a coordinate system relative to the ultrasound transducer, compress data, and the like. The therapeutic radiation delivery mechanism is separated and delivered through a different delivery mechanism.

Figure 3:
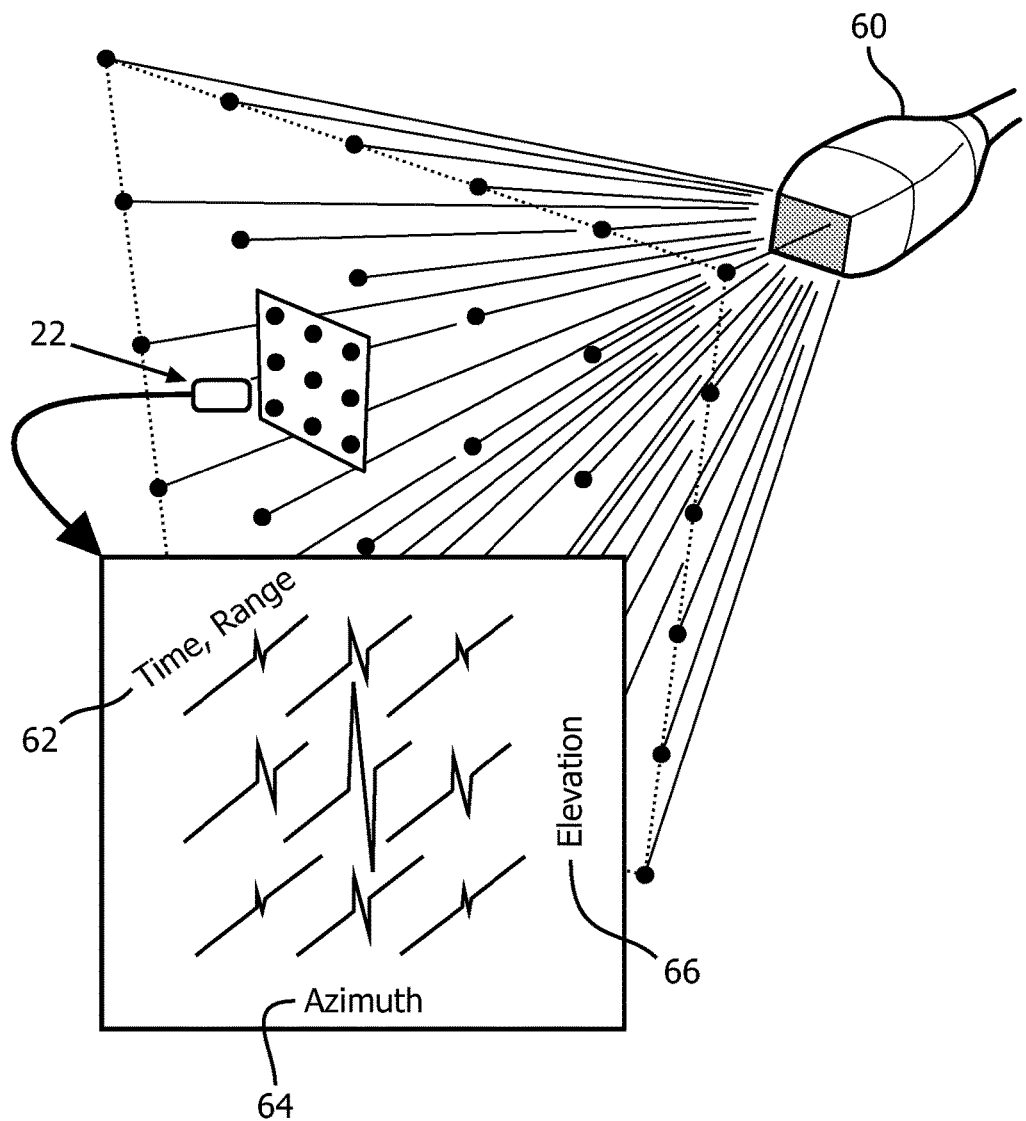
FIG. 3 diagrammatically illustrates an embodiment of the internal fiducial with a 3-dimensional (3D) ultrasound transducer.

With reference to FIG. 3 an embodiment of the internal fiducial 22 with a 3-dimensional (3D) ultrasound (US) transducer 60 is diagrammatically illustrated in perspective. The US transducer emits US sound waves of a predetermined frequency, direction, and time. The emitted waves based on direction can be received by the sensor 50 of the fiducial 22. Based on the time between emission and receipt, a range 62 can be computed. An azimuth 64 or lateral angle is computed based on the direction of one or more emitted US sound waves and the amplitude of the received sound wave. In the 3-D US, an elevation 66 is computed based on the direction of one or more emitted US sound waves and the intensity or amplitude of the received US sound wave. The individual emitted US sound waves are differentiated by timing in a firing sequence, frequency, or frequency encoding to provide time and/or directional encoding. As described in reference to FIGS. 2A and 2B, local processing can be performed by the circuitry located in the fiducial 22, and/or in the processor 32 located in the workstation 44 after receipt by the antenna 36 described in reference to FIG. 1.

Figure 4:
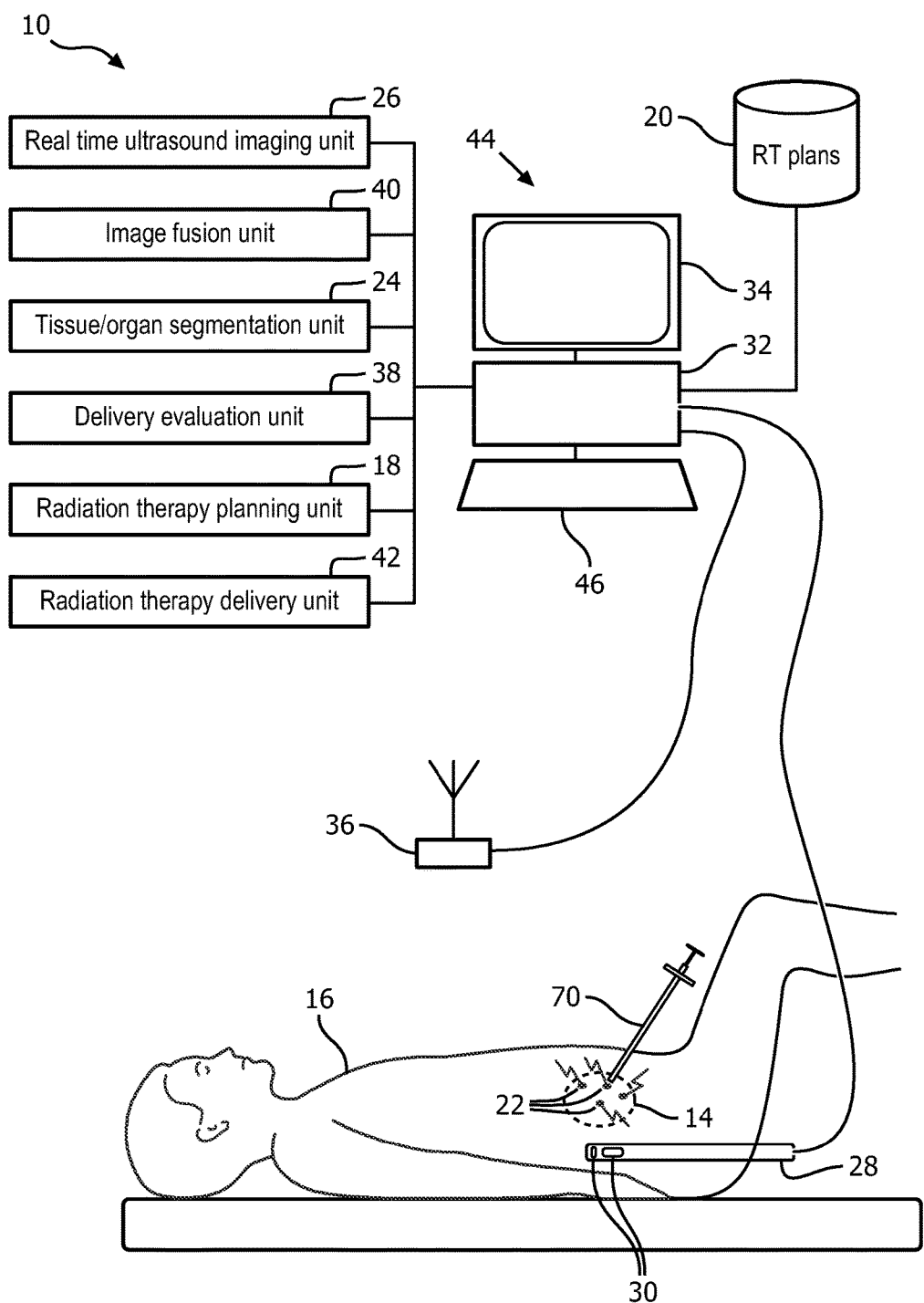
FIG. 4 schematically illustrates an embodiment of the real-time fusion of anatomical ultrasound information and radiation delivery system configured for brachytherapy.

With reference to FIG. 4, an embodiment of the real-time fusion of anatomical ultrasound information and radiation delivery system 10 configured for brachytherapy is schematically illustrated. The fiducials 22 are configured as described in reference to FIG. 2A which include radiation point sources 56. The ultrasound probe 28 is a trans-rectal ultrasound (TRUS) probe applied internally or inserted into a rectum of the subject in close proximity to the prostate for imaging the prostate region. The radiation plan 20 includes the planned placement of each radiation point source 56 relative to the target tissues. The radiation delivery mechanism includes a needle 70 which delivers the fiducials 22 with the radiation point sources 56 into the target locations. The needle 70 can be configured with a miniature transducer in the needle tip visible in the continuous real-time ultrasound images.

The continuous real-time ultrasound imaging unit 26 can project the target locations or planned placement of each point source onto the anatomic image displayed in the displayed ultrasound images. The planned placement can guide the healthcare practitioner in the placement of each seed. The ultrasound imaging unit 26 overlays the locations of the fiducials in the anatomic images based on the fused coordinate system. The locations can be color contrasted, identified with icons such as ellipses, crosses or other shapes, or otherwise identified in the images displayed on the display device 34.

The delivery evaluation unit 38 identifies the locations and the amounts of delivery therapeutic radiation assigned to each point source. The delivery evaluation unit can construct a dose cloud which accumulates the dose of all the point sources in a 3-D format.

The image fusion unit 40 fuses the locations of the fiducials in the first coordinate system of the ultrasound anatomic images with the second coordinate system of the therapeutic radiation delivery. The image fusion unit 32 fuses the second coordinate system of the delivered therapeutic radiation based on the close proximity of the therapeutic radiation point sources to the corresponding fiducial 26. The location of the fiducials are tracked by the image fusion unit 40 which tracks the movement of the fiducials through all types of motion including rigid, non-rigid, prostate deformation, and repetitive movement due to respiration and/or cardiac cycles.

The radiation therapy delivery unit 42 compares the actual placement of the therapeutic radiation with the radiation therapy plan. The comparison can include differences in radiation point sources which indicate the variance from a planned position to an actual position. The variance can include a change in therapeutic radiation amount or intensity. The radiation therapy delivery unit tracks which point sources are delivered and which are outstanding. The radiation delivery unit can compare the delivered therapeutic radiation to the planned therapeutic radiation delivery. For example, differences between the 3D actual dose cloud and the 3D planned dose cloud can be superimposed on the continuous real-time ultrasound images. Alternatively, the 3D dose cloud can be computed for effect on each segmented tumor or unhealthy tissue, and/or each segmented healthy tissue such as OARs. Another alternative includes superimposing both the 3D planned dose cloud and the 3D actual dose cloud on the continuous real-time ultrasound images.

The radiation therapy planning unit 18 can provide "what-if" simulations of changes in positions of planned radiation point sources and delivered radiation point sources. A visual display of the resulting dose cloud can superimposed on the segmented unhealthy tissue and/or segmented healthy tissues. During implantation of the seeds, the resulting dose cloud can be displayed as an overlay on the continuous real-time ultrasound images.

Figure 5:
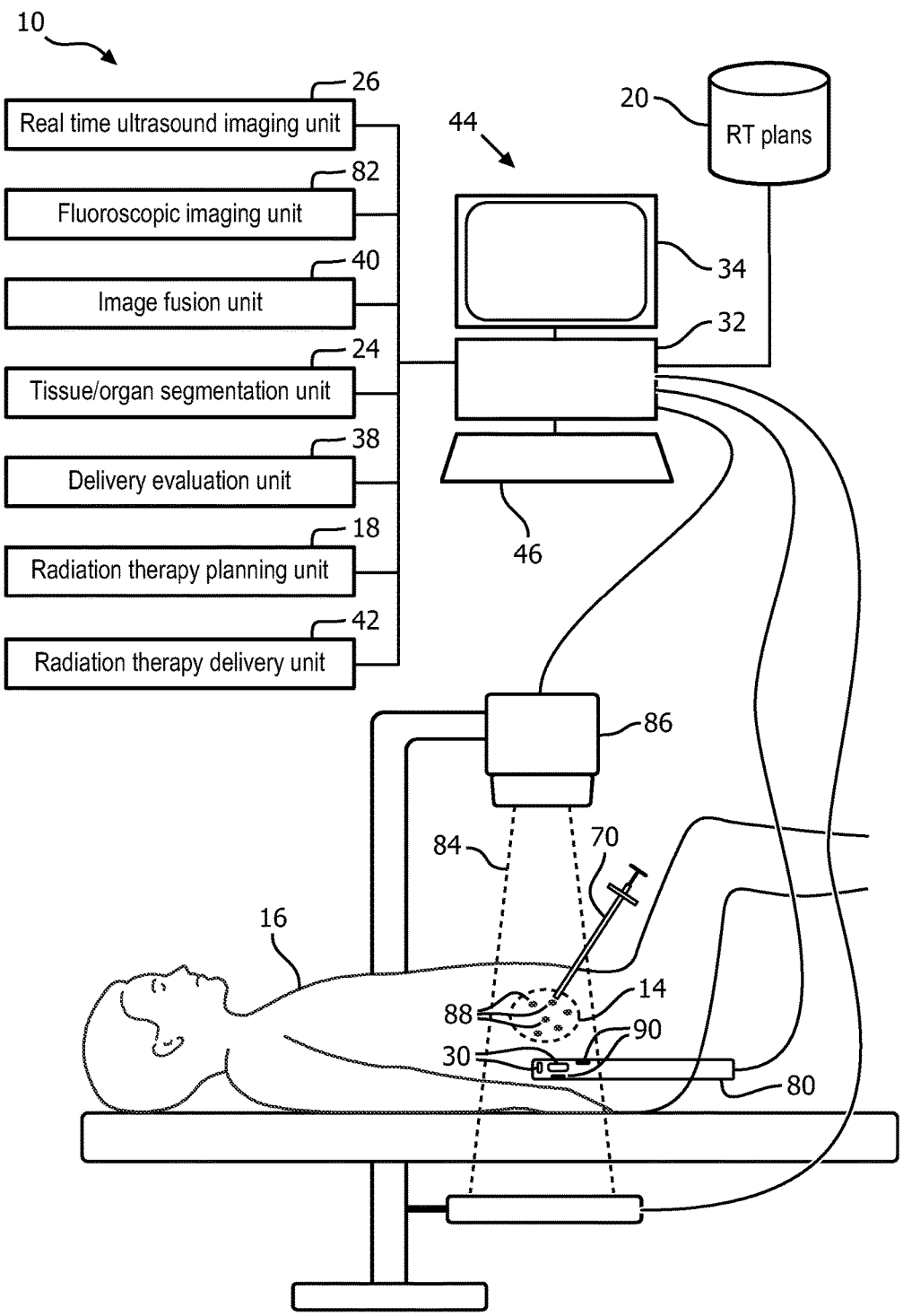
FIG. 5 schematically illustrates an embodiment of the real-time fusion of anatomical ultrasound information and radiation delivery information system configured for brachytherapy with a trans-rectal ultrasound (TRUS) probe.

With reference to FIG. 5, an embodiment of the real-time fusion of anatomical ultrasound information and radiation delivery information system 10 configured for brachytherapy with a TRUS probe 80 is schematically illustrated. A fluoroscopic imaging unit 82 includes the processor 32 programmed to generate fluoroscopic images of objects in a field-of-view (FOV) 84 of a fluoroscopic imaging device 86. The fluoroscopic imaging device 86 operates on demand or intermittent basis to reduce the imaging radiation exposure to the subject 16. The fluoroscopic imaging device is positioned with the FOV to include dropped seeds or radiation point sources 88 in the anatomic region such as the prostate, and fiducials 90 that are separated from the therapeutic radiation and included in the TRUS probe 80.

The fiducials 90, which include radio-opaque material can be embedded into the shaft, or affixed in a cover of the shaft such as a disposable sleeve configuration. The fluoroscopic imaging unit images the dropped seeds and the fiducials in the coordinate system of the fluoroscopic imaging device. The dropped seeds and the radio-opaque fiducials have high contrast in the fluoroscopic images. The real-time ultrasound imaging unit 26 is registered with the fiducials positioned in the probe and images the anatomic region, which includes the radiation point sources 88.

The radiation therapy delivery mechanism for the brachytherapy radiation point sources 88 includes the needle 70 inserted into the anatomic portion of the subject and drops seeds containing therapeutic radiation point sources. The target locations for the dropped seeds include predetermined locations based on the radiation therapy plan 20.

The image fusion unit 40 fuses the coordinate system of the fluoroscopic device and the coordinate system of the real-time ultrasound imaging unit and, in some embodiments, the coordinate system of the planning image. The image fusion unit can register the planning image to the ultrasound images. The fused coordinate system registers the locations of the radiation point sources 88 to the real-time ultrasound anatomic images.

The delivery evaluation unit 38 receives actual seed locations according to the coordinate system of the fluoroscopy unit and assigned dose values for each point source of therapeutic radiation. The delivery evaluation unit determines the actual anatomic locations of the actual delivered therapeutic radiation based on the fused coordinate system. The delivery evaluation unit can determine the amount and location of therapeutic radiation delivered to each of the target and OARs based on the fused coordinate system of the fluoroscopy unit and ultrasound.

Figure 6A:
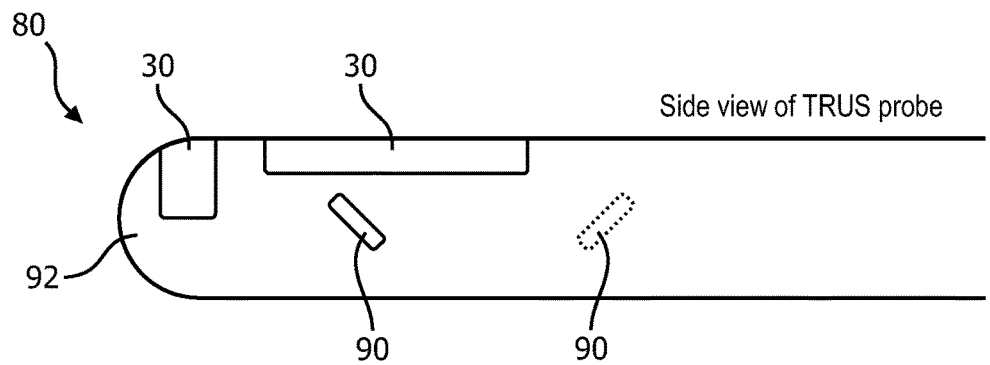
FIGS. 6A-6D schematically illustrates embodiments of the trans-rectal ultrasound (TRUS) probe with radio-opaque fiducials.
Figure 6B:
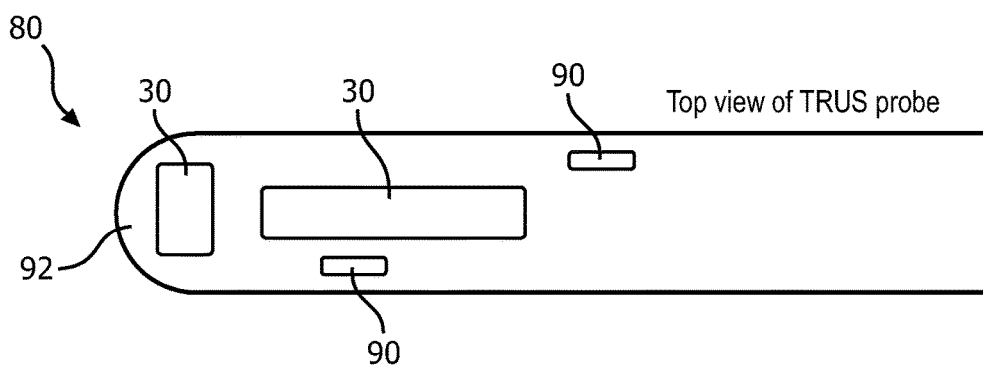

With reference to FIG. 6A, an embodiment of the TRUS probe 80 is schematically illustrated in a side view and with reference to FIG. 6B, the TRUS probe 80 is schematically illustrated in a top view. The TRUS probe includes a cylindrical shaft with a rounded end configured for insertion into the rectum of the subject. The shaft is constructed of a radio-transparent or radio-translucent material and the material is biocompatible.

The TRUS probe 80 includes in a 3D imaging configuration such as two imaging arrays 30 located on the cylindrical shaft 92 and oriented orthogonally to each other. Other configurations of imaging arrays are contemplated. The imaging arrays 30 include transducers which emit the ultrasonic sound waves.

The fiducials 90 can be embedded in the shaft 92 or included in a thin coat fitted over the TRUS probe 80. The fiducials 90 are radio-opaque in contrast to the shaft material. The fiducials can include one or more geometric objects positioned in different orientations to provide a three dimensional coordinate reference. The fiducials are calibrated to the imaging arrays on the probe of the ultrasound imaging unit.

Figures 6C, 6D:
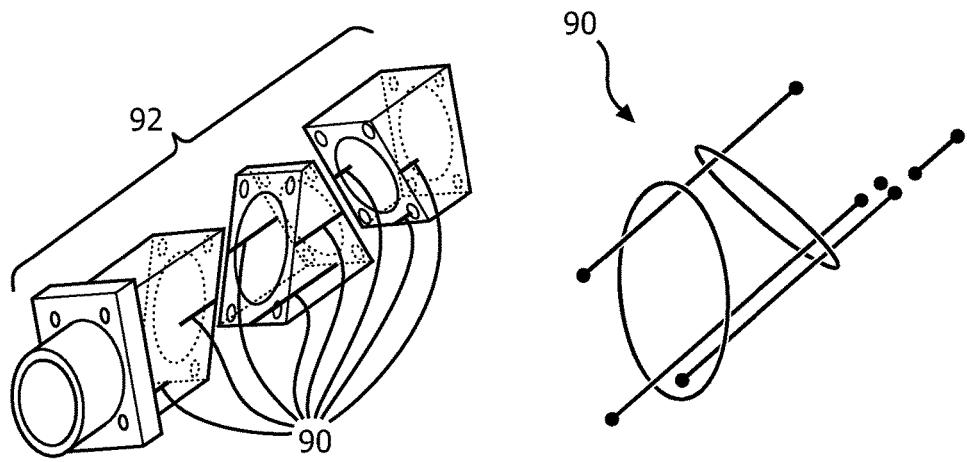

With reference to FIG. 6C, an intermediate stage of manufacturing the shaft 92 is schematically illustrated in perspective which shows the fiducials 90 embedded in the shaft. The shaft is shown in pieces angled oblique to a central axis. Fiducial rings are embedded in the shaft as rings on a joining surface between pieces. Lines and/or points are added to an inside or outside surface which run parallel to the central axis. The pieces with the radio-opaque material are joined to form the shaft and then the shaft is rounded.

With reference to FIG. 6D, the fiducials corresponding to FIG. 6C are shown as imaged in the fluoroscopic image. The fiducials include radio-opaque geometric shapes in different orientations. The shapes can include points, lines, ellipses, helicies, rings and/or curved shapes. Calibration of the probe 80 can be derived from the manufacturing specifications and/or computer-aid-design (CAD) sketches of the fiducial attachment. Additional fiducial shapes provide most robust calibration.

Figure 7:
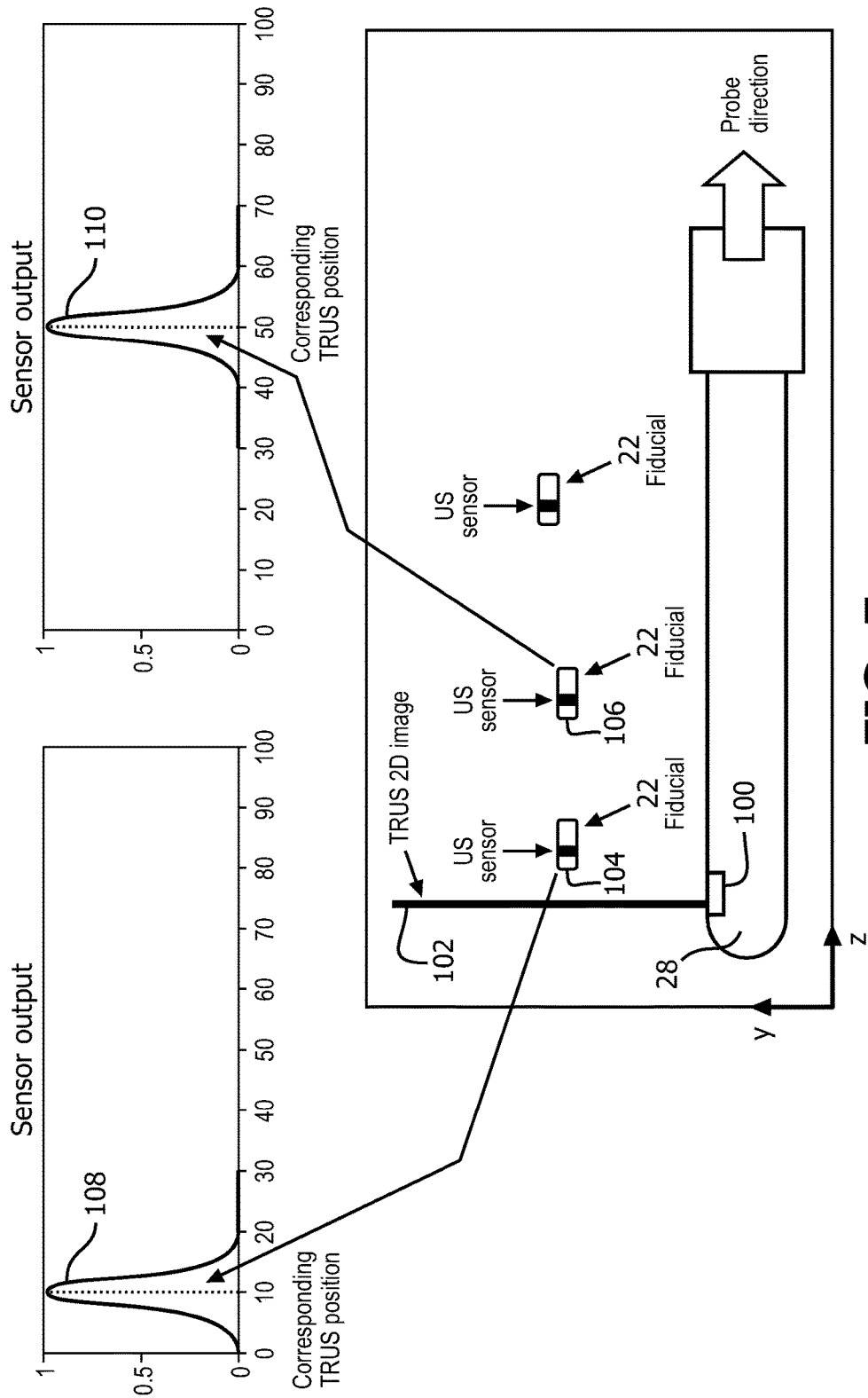
FIG. 7 diagrammatically illustrates an embodiment of the internal fiducial with a 2-dimensional (2D) ultrasound transducer.

With reference to FIG. 7 an embodiment of the internal fiducial 22 with a 2-dimensional (2D) ultrasound transducer 100 in a probe 28 and tracked movement of the transducer to provide three dimensional coordinates. The diagram illustrates how the 3D position of multiple fiducials 22 can be estimated with a 2D US probe 28. The probe includes a transducer 100. For example, as a 2D US imaging plane 102 moves in the z direction, the imaging plane encounters a first fiducial 104 and a second fiducial 106. As the ultrasonic waves in the plane encounter the fiducial, the fiducial transmits. The axial position indicates the z-direction for the first fiducial 104 in a graph 108 at axial position 10 mm and the second fiducial 106 in a second graph 110 at axial position 50 mm. The axial position is based on tracked movement of the TRUS probe. The 2D position of the fiducial is estimated in the 2D US image and the $3^{rd}$ coordinate of the fiducial is provided by the translational position of the TRUS probe. The tracked movement of the probe is included in the probe device or ultrasound imaging unit. The probe is moved by axial movement or movement into or out of the rectum. Thus, the coordinate system of the US imaging unit can operate with a 2D or 3D ultrasound probe and provide the location of the fiducials in a 3D coordinate system. Locations of fiducials not in the current 2D view can be tracked and the positions noted with different representations on images. For example, fiducials in a higher elevation can be represented differently such as a different color and/or shape from fiducials in the current imaging plane. Fiducials in a lower elevation can be represented as yet another color and/or shape.

Figure 8:
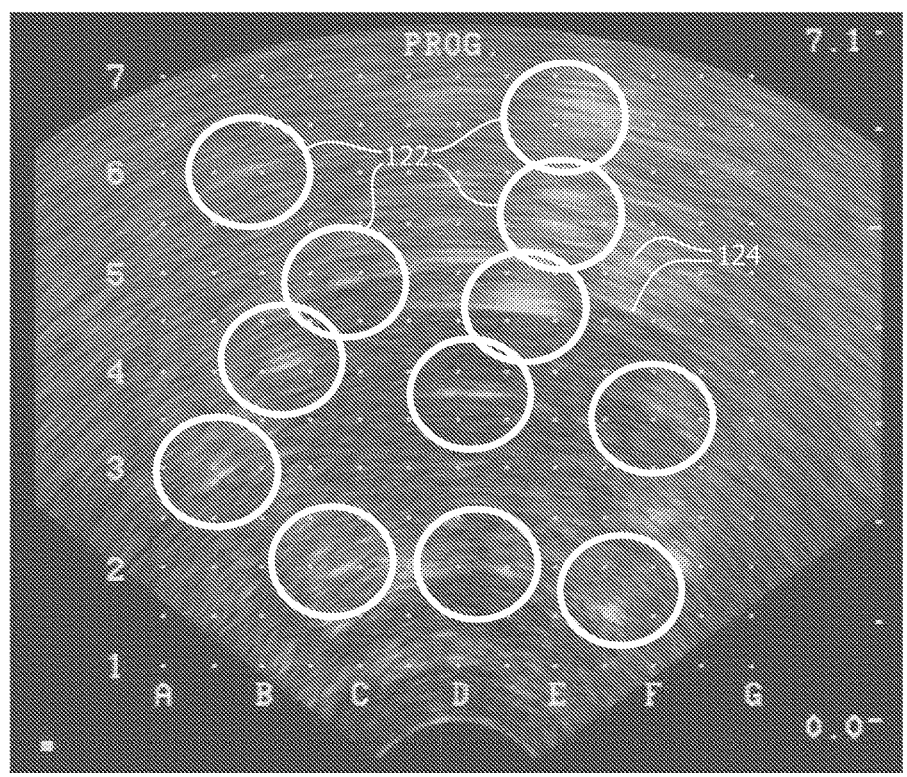
FIG. 8 illustrates an exemplary ultrasound image for brachytherapy with therapeutic radiation indicator.

FIG. 8 illustrates an exemplary ultrasound image 120 for brachytherapy with therapeutic radiation indicators 122 as ellipses. The example is of the portion of the prostate with brachytherapy radiation point sources. The delivery evaluation unit 38 identifies the locations of the radiation point sources 56, 88 based on the fused location of the fiducials 22, 90 by the image fusion unit 40. The example illustrates the problem of correctly identifying the radiation point sources with artifacts 124 confusingly similar to a radiation point source.

The locations of the fiducials 22 with corresponding point sources are updated in continuous real-time. The representative identification of the point sources can be a system and/or user preference. The preference can indicate a shape and/or color. Preferences can include a directional indicator such as color coding, dotted lines, shading, or other directional indicator that indicates whether the location is elevated above or below the current imaging plane.

In the embodiment of the system 10 describe in reference to FIG. 5, the locations of the radiation point sources are based on the most recent fluoroscopic image. The image can be presented without the identifiers, e.g. ellipses. In another embodiment, the healthcare practitioner can select a location on the image with the input device 46 to express clinical doubt. The system 10 responds with a response indicating the presence or absence of a radiation point source, e.g. "seed present" or "no seed". Alternatively, the response can include a distance and/or probability measure. The response is based on the location of the point source according to the fused coordinate system updated with the most recent fluoroscopic image. The update can include position based on tracking of the point sources among the intermittent fluoroscopic images and measures of periodic motion such as the respiration and/or cardiac cycles. Seed locations can be added to the fiducials of the TRUS probe to improve the registration between images.

Figure 9:
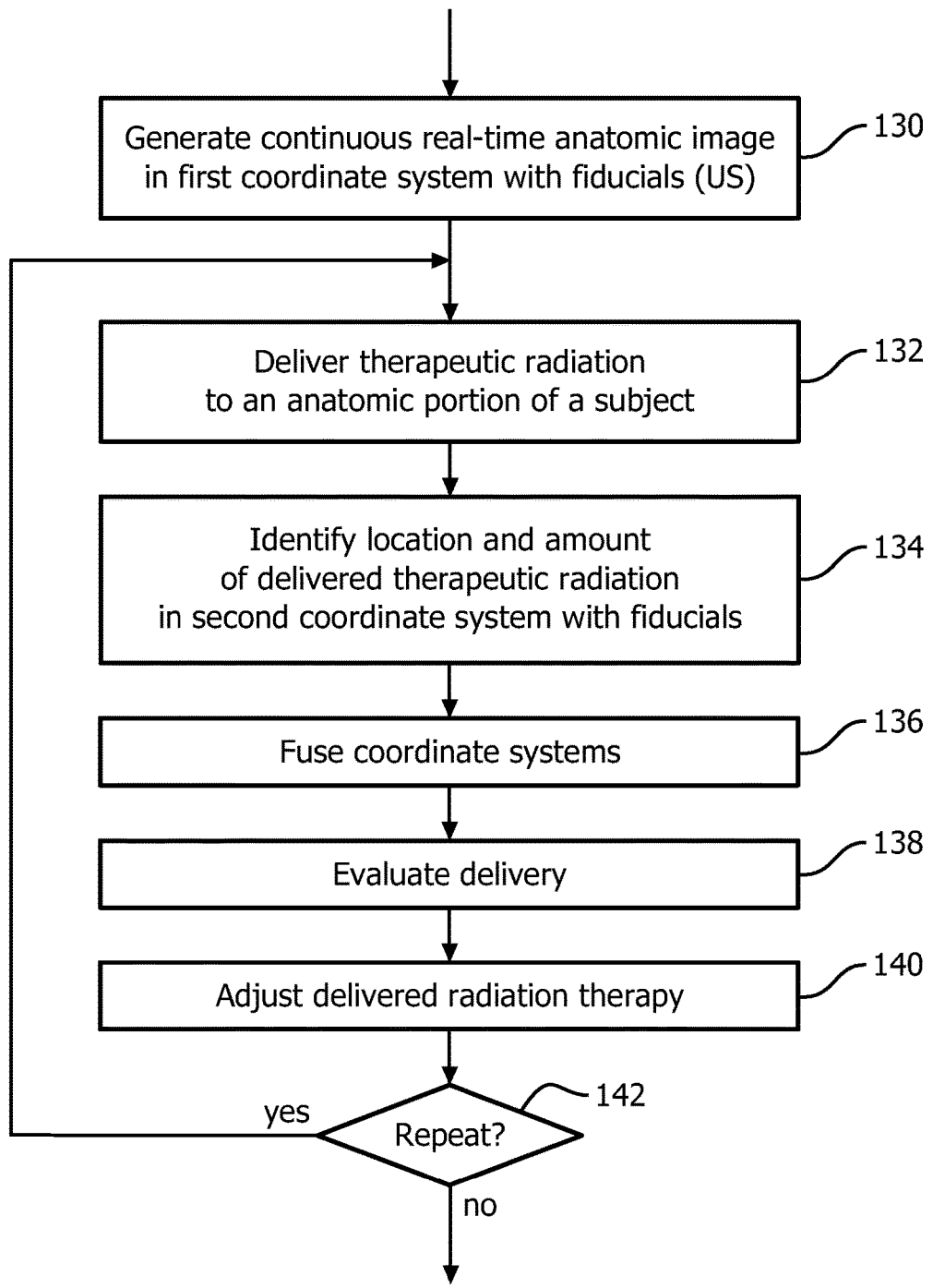
FIG. 9 flowcharts one method of real-time fusion of anatomical ultrasound information and radiation delivery information for interventional radiation therapy.

With reference to FIG. 9, one method of real-time fusion of anatomical ultrasound information and radiation delivery information for interventional radiation therapy is flowcharted. In a step 130, continuous real-time ultrasound images are obtained in a first coordinate system of an anatomic region of a subject with fiducials internal to the subject. The images are generated with an US probe which includes at least one transducer which emits ultrasonic sound waves. The US probe can be applied to the subject internally or externally. The location of the internal fiducials, in some embodiments, are implanted in and/or around target tissues, and locations determined by a self-identity transmitted in response to received ultrasonic sound waves which activate and power the wireless transmitter. The internal fiducials that are implanted, can include fiducials implanted in and/or around OARs. The implanted fiducials provide motion tracking of the tissues nearby. The activation of the implanted fiducial is based on a piezoelectric material of the fiducial, which converts the received ultrasonic sound waves into electrical current. The location relative to the probe can be determined based on the firing sequence of the ultrasonic sound waves and/or frequency of the sound waves as described in reference to FIGS. 3 and 7. In other embodiments, the internal fiducials are included as part of the internal probe. The fiducials affixed to or embedded in the probe are calibrated to the probe and the ultrasound coordinate system. In some embodiments, the internal fiducials are both implanted and included as part of the internal probe.

The step can include identifying by segmentation target tissues in the anatomic region, e.g. tumors, diseased tissue, and the like, according to the segmented planning image. The step can include tissue deformation and movement analysis using the fiducials as a reference. The movement analysis can include repetitive movement such as respiratory and/or cardiac motion, rigid motion such as patient body movement, non-rigid motion such as muscle flexing/relaxing, movement of the probe, movement of a subject support, etc.

Therapeutic radiation is delivered in amounts and locations according to the radiation therapy plan 20 in a step 132 in a second coordinate system. For example, EBRT beams of a shape, duration, intensity, and direction are projected in a coordinate system of the EBRT device and/or brachytherapy point sources of measured amounts of therapeutic radiation are inserted into tissues in a coordinate system of a healthcare practitioner instrument for dropping seeds. In a step 134, the fiducials in the second coordinate system are identified. The location of the fiducials can be identified either based the fiducials wirelessly transmitting at least a self-identity and/or based on radio-opaque material in an intermittent fluoroscopic image. The internal fiducials can be combined with the therapeutic radiation delivery, e.g. incorporated into capsules with the radiation point sources.

The fiducials can be separated from the therapeutic radiation delivery, e.g. separate implantation and/or included on internal probe.

The coordinate system of the real-time ultrasound imaging system, which includes the anatomic information, is fused with the coordinate system of the therapeutic radiation delivery based on the fiducials in a step 136. The fused coordinate system brings the anatomic information of the real-time ultrasound system into a common coordinate system with the therapeutic radiation delivery information. The fused coordinate system tracks the location of the fiducials relative to the anatomic information and the delivery of therapeutic radiation.

In a step 138, the locations and amounts of radiation delivered real-time to the anatomic region are evaluated based on the fused coordinate system. The evaluation can include segmenting the target tissues, e.g. tumors, and the OARs based on the planning image. Therapeutic radiation can be accumulated by voxel location in each segmented structure with the internal fiducials as reference. The therapeutic radiation dose can be accumulated for multiple modes of therapeutic radiation delivery, e.g. point sources of brachytherapy, beams of EBRT, and the like. The therapeutic radiation dose can be accumulated across treatment fractions. The evaluation can include a comparison of actual delivery with the radiation therapy plan 20.

The delivered radiation therapy can be adjusted in a step 140 during the treatment session. The adjustment can include the addition and/or placement of additional radiation point sources. The adjustment can include the modification of the external beam of therapeutic radiation in shape, duration, timing, direction, or intensity. For example, the beam can be gated on/off or the leaves of the MLC moved timed with the movement of the fiducials and the corresponding target or OARs.

In a step 142, a decision step continues the method repetitively in real-time during a treatment session or terminates at the end of the session based on the healthcare practitioner command entry with the input device.

Figure 10:
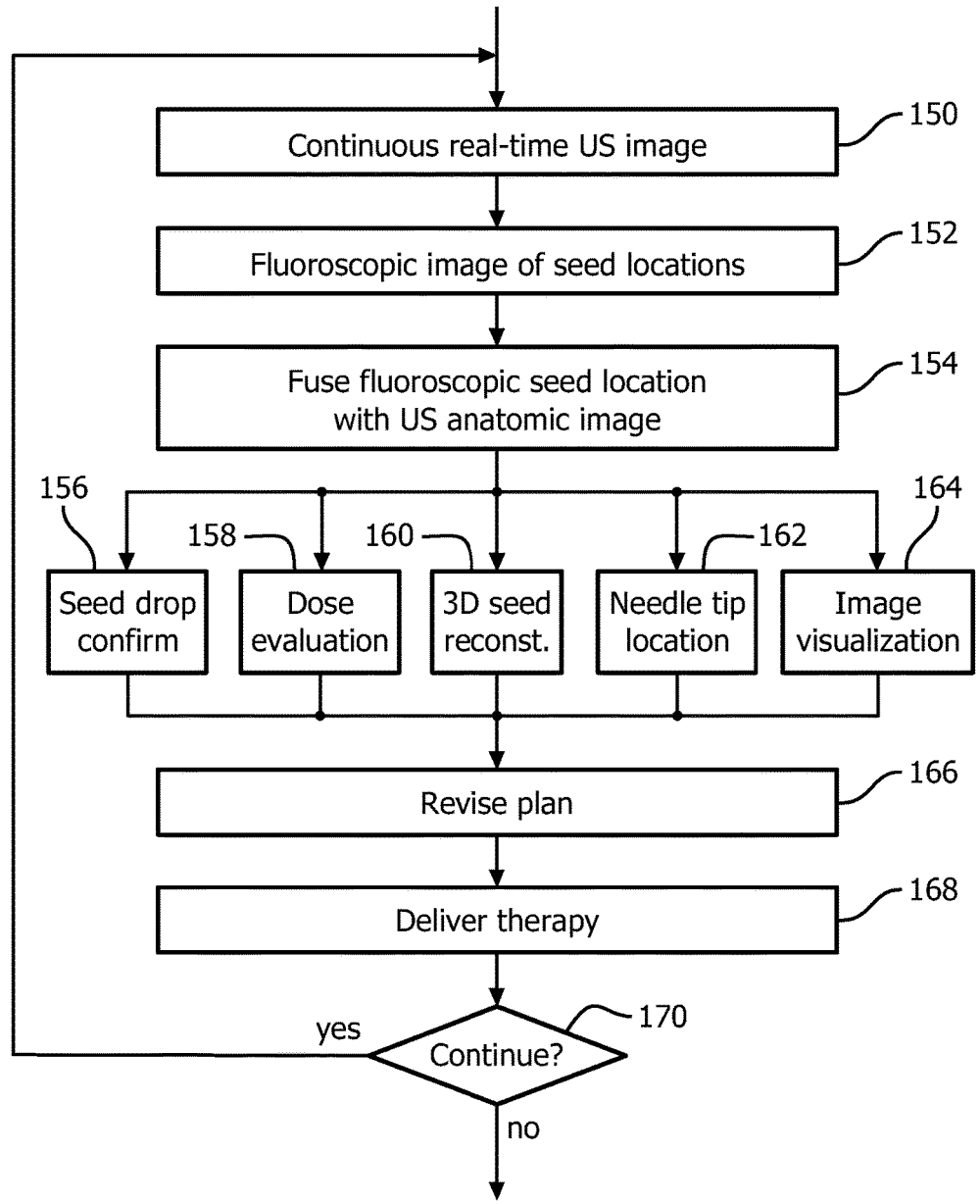
FIG. 10 flowcharts one method of using an embodiment of the real-time fusion of anatomical ultrasound information and radiation delivery information for brachytherapy with a TRUS probe.

With reference to FIG. 10, one method of using an embodiment of the real-time fusion of anatomical ultrasound information and radiation delivery information system 10 for brachytherapy with the TRUS probe is flowcharted. In a step 150, continuous real-time ultrasound images of an anatomic portion of a subject are obtained in a first coordinate system calibrated to fiducials located internally to the subject. The TRUS probe includes the calibrated fiducials. The continuous real-time ultrasound system can include the 2D or 3D probes described in reference to FIGS. 3 and 7. The step can include segmenting target tissues and/or OARs based on the planning image. The target and OAR structures can be identified in the images displayed on the display device.

In a step 142, the fluoroscopic image is obtained of the anatomic portion of the subject with radiation point sources or seeds and the fiducials in the field of view according to a coordinate system of the fluoroscopic imaging unit. The fluoroscopic image can be triggered by command entry from the healthcare practitioner using the input device. The imaging unit can alternatively substitute the most recent image or any previous image based on the tracked position of the fiducials corresponding to the position in the previous image. The fluoroscopic imaging can be triggered anytime such as after seeds from each needle are implanted, or after seeds from all needles implanted.

The coordinate system of the real-time ultrasound imaging of the anatomic portion of the subject is fused to the fluoroscopic coordinate system of the therapeutic radiation delivery or radiation point sources based on the fiducials in a step 154. For example, the planning image and delivery images can be registered based on organ contours. The registration of the continuous real-time ultrasound images to the fluoroscopic images can be improved based on the location of any delivered seeds and/or the location of the needle if equipped with a miniature transducer at the tip which makes the needle visible in the ultrasound. The needle and the seeds contrast in the fluoroscopic images.

In steps 156 through 164 the delivery of the therapeutic radiation is evaluated. The evaluation can include any one of a seed drop confirmation or seed location confirmation in step 156, dose evaluation in step 158, 3D seed reconstruction in step 160, needle tip location in step 162, or image visualization in step 164. In step 156, the presence of a seed or seed location is confirmed. The process can include automatic identification by segmenting the fluoroscopic image, or based on a request command entry by the healthcare practitioner. The request command entry can include selecting with the input device, e.g. mouse, an area on the displayed continuous real-time ultrasound image and receiving a response from the system regarding the presence or absence of the seed. The response can include a distance measurement based on the selected point in the image and/or a confidence measure such as a confidence interval, standard deviation, etc. The distance measurement can include motion measurement based on the previous imaged repetitive motion of the subject.

Dose evaluation includes actual delivered radiation based on the seeds present and assigned radiation values. Dose evaluation can include a comparison with the radiation therapy plan 20 such as difference between planned dose and actual dose, differences by segmented tissue, and/or superimposing actual and planned dose amounts. The displayed evaluation can be selectable by the healthcare practitioner for a selected location and/or structure, or displayed superimposed on the ultrasound and/or fluoroscopic images.

3D seed reconstruction includes locating existing seeds. 3D seed reconstruction can include identifying planned seed locations relative to the existing seed locations. 3D seed reconstruction can include location of seeds relative to segmented structures. Needle tip location includes locating the needle tip of the radiation point source delivery mechanism or other instrument in the fused coordinate system.

Image visualization includes combining for display information from the continuous real-time ultrasound with information from the fluoroscopic imaging. For example, segment structures can be outlined or colored coded in the image display, seed locations can be indicated with identifiers, dose levels and/or comparisons indicated, etc. Image visualization can include orienting the images in the coordinate reference of the fluoroscope, orienting the images in the coordinate reference of the continuous real-time ultrasound images, or another selected perspective such as the position of the needle or healthcare practitioner visual orientation to the subject.

In a step 166, the radiation therapy plan can be adjusted based on the evaluation steps. For example, the target location for implantation of remaining radiation point sources can be relocated and/or additional target locations identified. The adjustments form a revised radiation therapy plan which can then be re-evaluated in another iteration.

The radiation therapy treatment delivery continues, in a step 168, with the dropping or placement of additional seeds in target areas according to the radiation therapy plan with any revisions. The method continues with a decision step 170 which iterates the steps until the therapeutic radiation delivery is completed or until terminated by the healthcare practitioner. The iterations occur in real-time during delivery of the therapeutic radiation.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A radiation therapy system, comprising:
   a plurality of fiducials locatable internal to a subject;
   an ultrasound imaging unit which includes a transducer configured to emit ultrasonic sound waves to image in real-time an anatomic portion of a subject in a real-time coordinate system;
   a radiation planning unit configured to use at least one radiation treatment planning image to identify planned treatment locations and planned amounts of therapeutic radiation to be delivered to anatomic portions of the subject in a planning coordinate system;
   an image fusion unit configured to register the real-time coordinate system to the planning coordinate system based on the locations of the internal fiducials and to track the locations of the fiducials in real-time; and
   a delivery evaluation unit configured to identify the locations of the fiducials and the amounts of delivered therapeutic radiation relative to the imaged real-time anatomic portion of the subject,
   wherein each of the plurality of fiducials includes;
      a wireless transmitter configured to transmit at least a self-identity;
      a sensor connected to the transmitter which includes a piezoelectric element activated in response to receiving the emitted ultrasonic sound waves and which powers the transmitter; and
      a capsule constructed of biocompatible material which encapsulates the wireless transmitter and the sensor;
   at least one antenna located external to the subject and configured to receive the transmitted self-identities; and
   wherein the deliver evaluation unit is configured to identify the locations of the fiducials based on the transmitted self-identities and the amount of radiation based on the radiation delivery mechanism; and
   wherein the image fusion unit is configured to determine the locations of the fiducials relative to the ultrasound transducer based on a time between emission and receipt of the ultrasonic sound waves, and a direction of one or more emitted ultrasonic sound waves and the amplitude of the received one or more emitted ultrasonic sound waves.

2. The system according to claim 1, wherein the radiation planning unit is configured to modify the planned amounts and/or planned locations of therapeutic radiation to be delivered to the anatomic portions of the subject based on the delivered therapeutic radiation.

3. The system according to claim 1, wherein the radiation planning unit is configured to adjust the planned timing of therapeutic radiation delivery based on the location of the fiducials.

4. The radiation therapy delivery system, according to claim 1, further including:
   a radiation therapy delivery system configured to deliver the amounts of therapeutic radiation to the anatomic portion of the subject in the planning coordinate system.

5. The system according to claim 1, further including:
   a display device configured to display the fiducial locations superimposed on the real-time imaged anatomic portion of the subject.

6. The system according to claim 4, further wherein:
   the radiation therapy delivery system further includes an external beam radiation therapy device; and wherein
   the delivery evaluation unit is further configured to receive the amount and location of therapeutic radiation delivered based on the beam shape, duration, and direction from the external beam radiation therapy device according to the second coordinate system, and determine the amount and location of therapeutic radiation delivered to each target tissue and one or more organs-at-risk.

7. The system according to claim 6, further including:
   a radiation therapy delivery unit configured to control the external beam radiation therapy device to deliver beams of therapeutic radiation of a shape, direction, intensity, and duration based on a treatment plan; and
   wherein the radiation planning unit is configured to at least one of:
   modify the treatment plan during delivery, gate the external beam, or adjust collimation of the external beam based on the location of the fiducials.

8. A radiation therapy system comprising:
a plurality of fiducials locatable internal to a subject, each of the plurality of fiducials including:
a wireless transmitter configured to transmit at least a self-identify,
a sensor connected to the transmitter, the sensor including a piezoelectric element activated in response to receiving ultrasonic sound waves and connected to the transmitter to power the transmitter,
a radioactive point source; and
a capsule constructed of biocompatible material which encapsulates the wireless transmitter, the sensor, and the radioactive point source;
an ultrasound transducer configured to emit and receive ultrasonic sound waves to image in real-time an anatomic portion of a subject and the fiducials in a real-time coordinate system;
one or more processors configured to:
use at least one radiation treatment planning image to identify planned treatment locations and planned amounts of therapeutic radiation to be delivered to anatomic portions of the subject in a planning coordinate system,
determine locations of the fiducials relative to the ultrasound transducer based on a time between emission and reception of the ultrasonic sound waves and a direction of one or more emitted ultrasonic sound waves and an amplitude of received one or more emitted ultrasonic sound waves,
register the real-time coordinate system to the planning coordinate system based on the locations of the internal fiducials and to track the locations of the fiducials in real-time, and
identify the locations of the fiducials based on the transmitted self-identities and the amounts of therapeutic radiation delivered by the radioactive point-sources relative to the imaged real-time anatomic portion of the subject; and
at least one antenna located external to the subject and configured to receive the transmitted self-identities and communicate the received self-identities to the processor.

9. An implantable fiducial, comprising:
a wireless transmitter,
a sensor and
a capsule,
wherein the wireless transmitter is configured to transmit self-identity and at least one of the following information: i) a frequency of ultrasound activation emitted at a predetermined angle as detected by the sensor, ii) an intensity of ultrasound activation as detected by the sensor, iii) a checksum for verifying the self-identity, and iv) an ultrasound cycle count for establishing a time currency for the transmission;
wherein the sensor is connected to the transmitter and includes a piezoelectric element which is activated in response to received emitted ultrasonic sound waves and which is configured to power the transmitter; and
wherein the capsule is constructed of biocompatible material which encapsulates the wireless transmitter and the sensor and is configured to be implanted in a subject through a needle inserted when inserted into a subject.

10. The implantable fiducial according to claim 9, further including a radioactive point source encapsulated with the wireless transmitter and the sensor in the capsule such that the implantable fiducial is useable for brachytherapy.

11. The implantable fiducial according to claim 9, wherein the transmitter is a radio frequency (RF) transmitter.

12. The implantable fiducial according to claim 9, wherein the wireless transmitter is configured to transmit the check sum for verifying the self-identity.

13. The implantable fiducial according to claim 12, wherein the wireless transmitter is further configured to transmit information identifying a frequency of the received ultrasonic sound waves and an angle of receipt of the received ultrasonic sound waves.

14. The implantable fiducial according to claim 13, wherein the wireless transmitter is further configured to transmit an amplitude of the ultrasonic sound waves received by the sensor.

15. The implantable fiducial according to claim 9, wherein the wireless transmitter is configured to transmit all of the following information: (i) a frequency of the ultrasonic sound waves received by the sensor, (ii) an amplitude of the ultrasonic sound waves received by the sensor, (iii) a check sum which verifies the self-identity, and (iv) an ultrasound cycle count to establish a time currency for the transmitted ultrasonic sound waves.

* * * * *